United States Patent [19]

Lányi et al.

[11] Patent Number: 4,788,217
[45] Date of Patent: Nov. 29, 1988

[54] PESTICIDAL CARBAMATES

[75] Inventors: Grörgy Lányi, Budapest; Lajos Nagy, Szentendre; Éva Somfai, Budapest; Valéria Dénes née Lustig, Budapest; Erzsébet Radvány née Hegedos, Budapest; Lészloó Pap, Budapest; Tamás Detre, Nagymaros; András Szegö; Mária Visnyovszky neée Bvez, both of Budapest, all of Hungary

[73] Assignee: Chinoin Gyogyszer es Vegyeszeti Termekek Gyara Rt., Budapest, Hungary

[21] Appl. No.: 901,448
[22] PCT Filed: Nov. 15, 1985
[86] PCT No.: PCT/HU85/00068
§ 371 Date: Jul. 21, 1986
§ 102(e) Date: Jul. 21, 1986
[87] PCT Pub. No.: WO86/03202
PCT Pub. Date: Jun. 5, 1986

[30] Foreign Application Priority Data

Nov. 23, 1984 [HU] Hungary ............... 4346/84

[51] Int. Cl.[4] ................ A01N 47/10; C07D 307/86
[52] U.S. Cl. ................... 514/469; 544/153; 549/470
[58] Field of Search ........ 549/470; 544/153; 514/234, 469

[56] References Cited

FOREIGN PATENT DOCUMENTS 6917884 6/1971 Netherlands .

Primary Examiner—Mary C. Lee
Assistant Examiner—Bernard I. Dentz
Attorney, Agent, or Firm—Herbert Dubno; Jonathan Myers

[57] ABSTRACT

The invention relates to new compounds of the Formula I

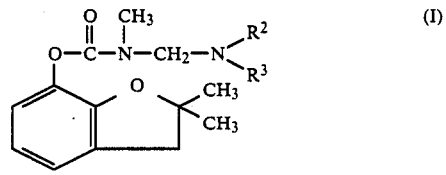

wherein
$R^2$ stands for hydrogen or $C_{1-4}$ alkyl; and
$R^3$ represents $C_{1-4}$ alkyl or a group of the Formula $R^4$—$(CH_2)_n$— wherein n is 1 or 2;
$R^4$ represents $C_1$ to $C_4$ alkoxy-carbonyl
or a group of the Formula II

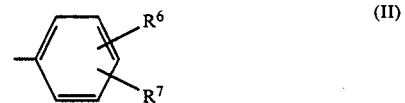

and
$R^6$ and $R^7$ stand for hydrogen or $C_{1-4}$ alkoxy; or
$R^2$ and $R^3$ together may form a group of the Formula —$(CH_2)_2$—O—$CH_2)_2$— with the proviso that $R^2$ and $R^3$ do not both stand for methyl, and salts thereof and a process for the preparation of the same.

17 Claims, No Drawings

PESTICIDAL CARBAMATES

This invention relates to new benzofurane derivatives, a process for the preparation thereof, pesticidal compositions comprising the same and the use of the said compositions for combating pests—particularly insects—and for inhibiting the growth thereof.

In the body of the specification and the set of claims the general symbols have the following definition:

$R^2$ stands for hydrogen or $C_{1-4}$ alkyl; and
$R^3$ represents $C_{1-4}$ alkyl or a group of the Formula
$R^4-(CH_2)_n-$, wherein
n is 1 or 2;
$R^4$ represents $C_1$ to $C_4$ alkoxy carbonyl or a group of the general Formula II, and
$R^6$ and $R^7$ stands for hydrogen or $C_{1-4}$ alkoxy; or
$R^2$ and $R^3$ together may form a group of the Formula
$-(CH_2)_2-O-(CH_2)_2-$.
with the proviso that $R^2$ and $R^3$ both do not stand for methyl.

It is known that the 2,3-dihydro-2,2-dimethyl-benzofurane-7-yl-methyl-carbamate (German Federal Republic patent No. 1 493 646) useful as a general soil disinfectant is a very toxic compound. In rats the acute toxicity amounts to $LD_{50}=8-10$ mg/kg p.o. For this reason the use of this compound is authorized only on industrial scale application.

It is the object of the present invention to provide new compounds which maintain the activity of the known derivatives but are less toxic.

It has been found that the new compounds of the Formula I

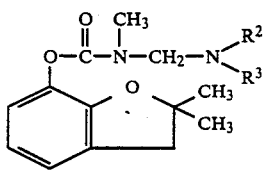
(I)

and salts thereof exhibit outstanding pesticidal—particularly insecticidal, acaricidal and nematodical—effect either per se or in combination with other compounds. The toxicity of the said new compounds is generally lower than that of chemically related known compounds. Moreover the compounds of the Formula I have a more simple structure, are less expensive and can be more readily prepared than the known derivatives having a satisfactory toxicity.

According to the present invention there are provided new compounds of the Formula I and salts thereof (wherein $R^2$ and $R^3$ are as stated above).

Preferable representatives of the compounds of the Formula I are the following derivatives:
2,3-dihydro-2,2-dimethyl-7-benzofuranyl-N-methyl-N-(N'-morpholinyl-methyl)-carbamate and salts thereof;
2,3-dihydro-2,2-dimethyl-7-benzofuranyl-N-methyl-N-[(N'-isopropyl)-N'-(β-carbethoxyethyl)-aminomethyl]-carbamate and salts thereof;
2,3-dihydro-2,2-dimethyl-7-benzofuranyl-N-methyl-N-[(β-3,4-dimethoxy-phenyl-ethyl)-amino-methyl]-carbamate and salts thereof;
2,3-dihydro-2,2-dimethyl-7-benzofuranyl-N-methyl-N-[(N'-(1,1-dimethyl-hydrazino)-methyl]-carbamate and salts thereof.

According to a further aspect of the present invention there is provided a process for the preparation of compounds of the Formula I and salts thereof, which comprises (a) reacting a compound of the Formula III

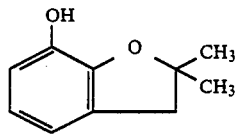
(III)

with a reactive derivative of an acid of the Formula IV; or

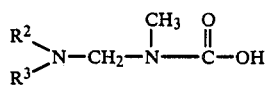
(IV)

(b) reacting a compound of the Formula V

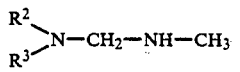
(V)

with a compound of the Formula VI, VII and/or VIII;

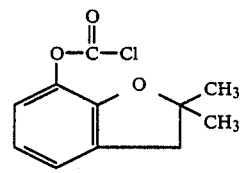
(VI)

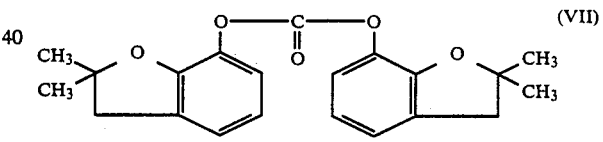
(VII)

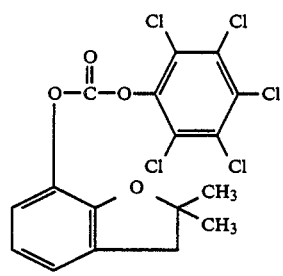
(VIII)

or (c) reacting a compound of the Formula IX

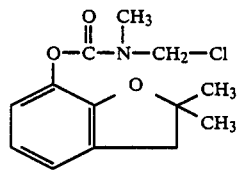
(IX)

with an amino of the Formula X

 (X)

and if desired converting the compound of the Formula I into a salt thereof.

According to method (a) of the process of the present invention a compound of the Formula III is reacted with a reactive derivative of an acid of the Formula IV. As reactive acid derivative an acid halide of the Formula XI

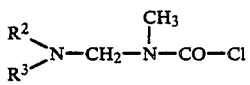 (XI)

or an anhydride of the Formula (XII

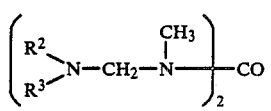 (XII)

or an active ester—preferably an ester of the Formula XIII—

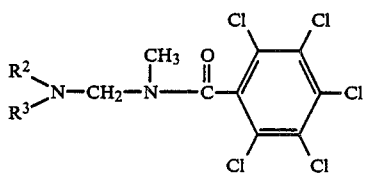 (XIII)

may be used.

The reaction may be preferably carried out in the presence of an aprotic solvent (e.g. benzene or toluene) and a tertiary base. As tertiary base e.g. a trialkyl amine may be used. The reaction may be accomplished preferably at a temperature between 10° C. and 30° C.

Method (b) of the process of the present invention may be preferably carried out under the same reaction conditions as method (a).

According to method (c) of the process of the present invention it is preferred to use as starting material a compound of the Formula IX, which is prepared by reacting 2,3-dihydro-2,2-dimethyl-7-benzofuranyl-methyl-carbamate with thionyl chloride and paraformaldehyde, preferably in the presence of an aprotic organic solvent. The 2,3-dihydro-2,2-dimethyl-7-benzofuranyl-methyl-carbamate may be prepared from benzofuranol of the Formula III by known methods, e.g. by reacting with methyl isocyanate.

The reaction according to method (c) may be preferably carried out in the presence of an aprotic organic solvent (e.g. benzene) at a temperature between 10° C. and 40° C. It is preferred to add a tertiary base to the reaction mixture.

The compounds of the Formula I may be converted into the salts thereof. Salt formation may be carried out by using inorganic or organic acids. The salts also exhibit the insecticidal, acaricidal and nematocidal effect of the bases of the Formula I.

According to a further aspect of the present invention there are provided pesticides—particularly compositions suitable for combating insects, mites and nematodes—comprising as active ingredient at least one compound of the general Formula I or a salt thereof.

The present invention encompasses all formulations comprising a compound of the Formula I or a salt thereof. This the present invention covers all compositions which comprise a compound of the Formula I or a salt thereof and a carrier and appear in this form on the market.

The invention extends also to ready-for-use preparations prepared from the above compositions by aqueous dilution; the latter compositions may be directly used in agriculture or in other environment where pests occur.

The compositions of the present invention may be excellently used for combating insects at any suitable stage of the growth of the insect. Thus the compositions are particularly suitable for combating house fly, granary weevils, flour beetle, plant louse, cabbage butterfly, plum beetle, Mexican bean beetle, sunflower beetle, pea louse, etc.

The compositions of the present invention are particularly useful as soil disinfectant and in greenhouses. The field of application of the said compositions is broadened by the systemic effect thereof.

The compositions of the present invention generally comprise additives in addition to the active ingredients. The said additives may be biologically active components or inert carriers and auxiliary agents which facilitate transport and storing and also synergists.

As further active ingredient insecticidal, nematocidal or acaricidal compounds having a different chemical structure or point of biological attack may be used. Thus fungicidal or plant growth regulating compounds or artifical fertilizers may be used.

The auxiliary agents are selected on the basis of the form in which the composition is intended to be used.

Thus suspension concentrates may comprise 1–60% by weight of an active ingredient of the Formula I or a salt thereof and 40–99% by weight of auxiliary agents suitable for the formation of a stable suspension concentrate. As auxiliary agent 1–10% by weight of a surfactant may be used. As preferable representatives of the surfactants the following compounds may be mentioned: alkyl phenol ethoxylates, polyoxyethylene alkylethers, polyoxyethylene fatty acid esters, polyoxyethylene fatty alcohol ethers, non-ionic adducts of calcium alkyl aryl sulfonate, ethoxylated esters and salts thereof, phosphatated esters and salts thereof, alkali and alkaline earth lignin sulfonates, condensation products of formaldehyde and sodium alkyl aryl sulfonates, adducts of cresol and formaldehyde, etc.

According to a preferred embodiment of the present invention there are provided dispersible granules comprising as active ingredient 1 to 99% by weight of a compound of the Formula I or a salt thereof in admixture with 99 to 1% by weight of an additive suitable for the formation of dispersible granules. As auxiliary agent preferably 0.1 to 1% by weight of an anionic and/or non-ionic surfactant, particularly one or more of the following agents may be used: alkali salts of alkyl and aryl sulfonic acids; alkali salts of condensation products of alkyl aryl sulfonic acids and formaldehyde, alkyl aryl polyglycol ethers; sulfated higher alcohols, polyethylene oxides; sulfated fatty alcohols; esters of fatty acids and polyglycols and various other commercially available surfactants.

According to a further preferred embodiment of the present invention there are provided granular compositions comprising preferably 1 to 20% by weight of a compound of the Formula I or a salt thereof as active ingredients in admixture with 80 to 99% by weight of an additive. For this purpose adhesives, coloring agents and/or carriers may be used. Suitable adhesives are the following compounds: polyvinyl alcohol, polyvinyl pyrrolidone, sugar, lignin sulfonates, polysaccharides and/or natural oils. As carrier e.g. sand, ground minerals, agricultural waste materials and products prepared thereof (e.g. furfurol bran) and other commercially available substances having large surface may be used.

According to a still further preferably embodiment of the present invention there are provided emulsion concentrates comprising preferably 10 to 50% by weight of a compound of the general Formula I or a salt thereof in admixture with 50 to 90% by weight of an additive suitable for the formation of a stable emulsion, when the emulsion concentrate is emulsified in or in the presence of water.

As additive e.g. 1 to 20% by weight of a tenside and/or 0.1 to 5% by weight of a stabilizing agent may be used and the mixture may be filled up to 100% by weight with an organic solvent.

As tenside a mixture of anionic and non-ionic tensides having a HLB value of 8-14 may be advantageously used. Thus the following tensides may be preferably applied: calcium salts of alkyl aryl sulfonic acids; mono- and diesters of phosphoric acid; nonyl and tributyl phenol polyglycol ethers; adducts of fatty alcohols and ethylene oxide; fatty acid polyglycol esters; ethylene oxide and propylene oxide block polymers, etc.

The following solvents may be used preferably for this purpose: mixtures of aromatic solvents (e.g. xylenes, cyclohexanol, butanol, methyl ethyl ketone, isopropanol, etc.).

The compositions of the present invention may also contain a stabilizer. For this purpose preferably compounds comprising an epoxide group (e.g. epichlorohydrin or edenol—epodised soya oil, etc.) may be used.

The compositions of the present invention may also comprise a synergist which enables the use of smaller amount of the active ingredient of the Formula I in the composition. The said additives are particularly useful in compositions which are applied onto the surface of the plant or sites being contacted with warm-blooded living organisms rather than onto the soil. As synergist preferably piperonyl butoxide may be used.

According to a still further aspect of the present invention there is provided a method for combating undesired insects, mites and/or nematodes which comprises contacting the said pests at any suitable stage of their growth with an effective amount of a compound of the Formula I or a salt thereof or a composition comprising the same.

The compositions of the present invention are particularly suitable as soil disinfectant or on the surface of the plants and may be successfully applied both in glasshouse and under field conditions.

Further details of the present invention are to be found in the following Examples without limiting the scope of protection to the said Examples.

EXAMPLE 1

104.7 g of 2,3-dihydro-2,2-dimethyl-7-benzofuranyl-methyl-N-chloromethyl-carbamate are dissolved in 600 ml of benzene. To the solution at room temperature and within an hour a solution of 37.7 g of morpholine, 43.8 g of triethyl amine and 50 ml of benzene is added. The reaction mixture is stirred for 2 hours whereupon 200 ml of water are added. The solid material goes into solution. The organic phase is separated, dried over sodium sulfate and the solvent is distilled off. Thus 120.1 g of 2,3-dihydro-2,2-dimethyl-7-benzofuranyl-N-methyl-N-(N'-morpholinyl-methyl)-carbamate are obtained. m.p.: 90°–91° C. The product is purified through the hydrochloride, m.p.: 92°–96° C.

Analysis: for the Formula $C_{17}H_{24}N_2O_4$

| calculated: | C = 63.75% | H = 7.50% | N = 8.75% |
| found: | C = 63.86% | H = 7.51% | N = 8.86%. |

EXAMPLE 2

40.5 g of 2,3-dihydro-2,2-dimethyl-benzofuranyl-N-methyl-N-chloromethyl-carbamate are dissolved in 250 ml of benzene. To the solution at room temperature within an hour a solution of 10.1 g of isopropyl amine, 17.2 g of triethyl amine and 50 ml of benzene is added. The reaction mixture is stirred for 2 hours and worked up as described in Example 1. Thus 30.4 g of 2,3-dihydro-2,2-dimethyl-7-benzofuranyl-N-methyl-N-/isopropyl-amino-methyl/-carbamate are obtained, mp.: 73°–76° C.

Analysis: for the Formula $C_{16}H_{24}N_2O_3$

| calculated: | C = 65.75% | H = 8.22% | N = 9.59% |
| found: | C = 66.01% | H = 8.07% | N = 9.68%. |

EXAMPLE 3

24.5 g of 2,3-dihydro-2,2-dimethyl-7-benzofuranyl-N-methyl-N-chloromethyl-carbamate are dissolved in 100 ml of benzene whereupon at room temperature within an hour a solution of 10.1 g of triethyl amine, 23.8 g of N-/β-carbethoxy-ethyl/-isopropylamine and 50 ml of benzene is added. The reaction mixture is worked up according to Example 1. Thus oily 2,3-dihydro-2,2-dimethyl-7-benzofuranyl-N-methyl-N-[(N'-isopropyl)-N'-(β-carbethoxy-ethyl)-amino-methyl]-carbamate are obtained.

Analysis: for the Formula $C_{21}H_{31}N_2O_5$

| calculated: | C = 64.37% | H = 7.92% | N = 7.15% |
| found: | C = 63.90% | H = 8.12% | N = 7.05%. |

EXAMPLE 4

13.5 g of 2,3-dihydro-2,2-dimethyl-7-benzofuranyl-N-methyl-N-[chloromethyl]-carbamate are dissolved in 100 ml of benzene, whereupon within an hour a solution of 12.8 g of 3,4-dimethoxy-β-phenyl-ethyl amine and 30 ml of benzene is added. The reaction mixture is worked up as described in Example 1. Thus 15.4 g of oily 2,3-dihydro-2,2-dimethyl-7-benzofuranyl-N-methyl-N-[3,4-(dimethoxy)-phenylethyl]-amino-methyl-carbamate are obtained.

Analysis: for the Formula $C_{23}H_{30}N_2O_5$

| calculated: | C = 66.66% | H = 7.25% | N = 6.76% |
| found: | C = 67.00% | H = 6.85% | N = 6.23%. |

EXAMPLE 5

53.8 g of 2,3-dihydro-2,2-dimethyl-7-benzofuranyl-N-methyl-N-chloromethyl-carbamate are dissolved in 250 ml of benzene. To the solution at room temperature within an hour a mixture of 15.25 g of 1,1-dimethylhydrazine, 25.25 g of triethyl amine and 50 ml of benzene is added. The suspension thus formed is stirred for 2 hours and filtered. Thus 51 g of 2,3-dihydro-2,2-dimethyl-7-benzofuranyl-N-methyl-N-[N'-(1,1'-dimethyl-hydrazino)-methyl]carbamate hydrochloride are obtained, mp.: 107°–110° C.

Analysis: for the Formula $C_{15}H_{24}ClN_2O_3$

| | | | | |
|---|---|---|---|---|
| calculated: | C = 54.63% | H = 7.28% | N = 12.75% | Cl = 10.77 |
| found: | C = 53.61% | H = 7.27% | N = 11.94% | Cl = 10.88 |

EXAMPLE 6

16.4 g of 2,3-dihydro-2,2-dimethyl-7-benzofuranol are dissolved in 50 ml of toluene whereupon 14.9 g of phosgene are introduced into the solution at a temperature of −5° C. within an hour. As acid binding agent 5N sodium hydroxide solution is added at a temperature between −5° C. and 0° C. at a rate that during addition the pH value should not be higher than 7. After an hour the toluene phase if separated, washed neutral with water, dried over sodium sulfate and the solvent is distilled off.

The residual 2,3-dihydro-2,2-dimethyl-7-benzofuranyl-chloro-formic acid ester are dissolved in 100 ml benzene. To the solution is added a solution of 15.6 g N-(morpholinomethyl)-methylamine and 12 g triethyl amine in 50 ml benzene at a temperature between +5° C. and +10° C. within an hour. The reaction mixture is worked up as described in Example 1. Thus 25.1 g 2,3-dihydro-2,2-dimethyl-7-benzofuranyl-N-methyl-N-[N'-(morpholinomethyl)]-carbamate melts at 92°–95° C. and is identical with the product obtained according to Example 1.

EXAMPLE 7

22.6 g 2,3-dihydro-2,2-dimethyl-7-benzofuranyl-chloro-formic acid ester are dissolved in 100 ml benzene. To the solution is added a solution of 29.3 g pentachloro benzene in 100 ml benzene. As acid binding agent 5N sodium hydroxide solution or triethylamine is added in an amount to adjust the pH to 7. The obtained benzene solution is washed neutral, and to the solution is added a solution of 14.3 g N-(morpholinomethyl)-methylamine and 11 g triethylamine in 50 ml benzene at a temperature of 20° C. within an hour. After mixing for 3 hours the reaction mixture is worked up as described in Example 1. Thus 2,3-dihydro-2,2-dimethyl-7-benzofuranyl-N-methyl-N-(N'-morpholinomethyl)-carbamate melts at 92°–96° C.

EXAMPLE 8

13 g of N-(morpholinomethyl)-methylamine are dissolved in 100 ml toluene whereupon 14.9 g phosgene are introduced into the solution at a temperature between −5° C. and 0° C. To the mixture containing N-methyl-N-(morpholinomethyl)-amino-carbonyl chloride a mixture of 15 g of 2,3-dihydro-2,2-dimethyl-7-benzofuranol, 10 g of triethylamine and 50 ml of benzene is added. The reaction mixture is worked up as described in Example 1. Thus 2,3-dihydro-2,2-dimethyl-7-benzofuranyl-N-methyl-N-(N'-morpholinomethyl)-carbamate melts at 92°–95° C. and is identical with the product obtained according to Example 1.

EXAMPLE 9

13 g of N-(morpholinomethyl)-methylamine are dissolved in 100 ml of toluene. Into the solution 7 g of phosgene are introduced at a temperature between −5° C. and 0° C. within an hour. As acid binding agent 5N aqueous sodium hydroxide solution is added in an amount to adjust the pH to 7. After 2 hours the toluene phase is washed neutral with water and to the solution comprising bis-[N-methyl-(N-morpholinomethyl)]-urea a solution of 15.8 g of 2,3-dihydro-2,2-dimethyl-7-benzofuranol, 10.1 g of triethyl amine and 50 ml of water is added at room temperature within an hour. The reaction mixture is washed neutral with water, the organic phase is separated, dried and the solvent is removed. The residue is dissolved in hydrochloric acid whereafter the salt is re-converted into the base alkalizing the solution. Thus 22.7 g of 2,3-dihydro-2,2-dimethyl-7-benzofuranyl-N-methyl-N-(N'-morpholinomethyl)-carbamate are obtained.

Mp.: 92°–96° C.

EXAMPLE 10

To a toluene solution of N-methyl-N-(morpholinomethyl)-amino-carbonyl-chloride a solution of 29.3 g of pentachloro phenol, 11 g of triethylamine and 100 ml of benzene is added. After 2 hours to the solution containing the pentachlorophenyl-N-methyl-N-(morpholinomethyl)-amino-carboxylate at room temperature within an hour a solution of 15.8 g of 2,3-dihydro-2,2-dimethyl-7-benzofuranol, 11 g of triethyl amine and 50 ml of toluene is added at room temperature within an hour. The reaction mixture is stirred at room temperature for 2 hours, treated with water, washed neutral, the organic solvent phase is separated, dried over sodium sulfate evaporated. The residue is converted into the sulfate with the aid of diluted sulfuric acid. On making the solution alkaline 123.1 g of 2,3-dihydro-2,2-dimethyl-7-benzofuranyl-N-methyl-N-(N'-morpholinomethyl)-carbamate precipitates, mp.: 92°–95° C.

EXAMPLE 11

In a mixture of 7 g of ethylene glycol and 52.6 g of water 4 g of Atlox 4862 are dissolved whereupon 35 g of 2,3-dihydro-2,2-dimethyl-7-benzofuranyl-N-methyl-N-(N'-morpholinomethyl)-carbamate are incorporated with the aid of a high shear strength desagglomerating stirrer (Ultra Turax 15N; 15 m/sec). The suspension thus obtained is ground in a cooled attritor (200 ml) in the presence of 100 ml of silicoquarzite glass pearls (diameter 2 mm) for 45 minutes at 750 r.p.m. To the ground material 2 g of Soitem 22 FL/N are added whereupon the glass pearls are removed by sieving through a sieve (mesh size 1.5 mm). To the suspension 0.2 g of Tensiofix 821 are added and incorporated with the aid of a Turrax 15N deagglomerating stirrer within 5 minutes. To the product 0.2 g of Tensiofix LO 51 antifoam agent are added. The particle size of the active ingredient of the composition thus obtained is below 5 μm 95% (measured by ultrasonic moist sieving), the floating capacity amounts to 90% (according to CIPAC) and the flow value is 52 sec (Ford No. 4 glass).

Preparations having the following composition are prepared:

| Component | Amount (% by weight) |
|---|---|
| Active ingredient | 1-60 |
| Anionic or non-ionic surfactant | 1-7 |
| Antifreezer | 5-10 |
| Antisedimentating agent | 0.1-0.5 |
| Antifoam agent | 0.1-0.5 |
| Water | ad 100 |

EXAMPLE 12

Dispersible granule

A mixture of 700 g of 2,3-dihydro-2,2-dimethyl-7-benzofuranyl-N-methyl-N-(N'-morpholinomethyl)-carbamate, 50 g of Atlox 4862, 50 g of Aerosil OTB, 10 g of Plasdon K 25 and 190 g of lactose is homogenized in a MTH KV-10 (Papenmeier) powder mixer for 2 minutes (1000 r.p.m.). The powder mixture is ground in an air-flow mill (IMRS-80) so that 90% of the particles should be smaller than 10 μm (measured by ultrasonic moist sieving).

10 g of the powder mixture thus obtained are contacted in a household coffee-mill with 1.2 ml of water to form granules (stirring period 20 seconds). The granules thus obtained are dried in vacuo at 50° C. The dried product is sieved (mesh size 0.1 and 1.0 mm). The floating capacity of the granules thus obtained amounts to 84% (measured by the CIPAC method).

Preparations having following composition are prepared:

| Components | Amount (% by weight) |
|---|---|
| Active ingredient | 1-99 |
| Synthetic silicic acid | 0.1-2 |
| Dispersing agent | 0.1-10 |
| Anionic and non-ionic surfactant | 0.1-5 |
| Adhesive macromolecule | 0.2-2 |
| Sugar | ad 100.0 |

EXAMPLE 13

Granules

5% by weight of 2,3-dihydro-2,2-dimethyl-7-benzofuranyl-N-methyl-N-[N'-(isopropyl)-N'-(β-carboethoxyethyl)-aminomethyl]-carbamate are admixed with 10% by weight of dimethyl formamide and 85% by weight of furfurol bran (particle size 0.2-1 mm).

The granules are of the following composition:

| Component | Amount (% by weight) |
|---|---|
| Active ingredient | 1-20 |
| Solvent | 3-10 |
| Carrier | ad 100 |

EXAMPLE 14

Emulsifiable concentrate

25% by weight of 2,3-dihydro-2,2-dimethyl-7-benzofuranyl-N-methyl-N-(isopropyl-aminomethyl)-carbamate are dissolved in 49% by weight of methyl ethyl ketone. To the solution 1% by weight of edenol (epoxidized soya oil) and 25% by weight of a mixture of emulsifiers are added.

The emulsifier mixture consists of the following components:

| ATLOX-4857 B | 15% by weight |
|---|---|
| ATLOX-3400 B | 10% by weight |
| SHELLSOL R | 62.5% by weight |
| Isopropanol | 12.5% by weight |

Preparations having the following composition are prepared:

| Component | Amount (% by weight) |
|---|---|
| Active ingredient | 10-50 |
| Ionic and non-ionic surfactant | 5-10 |
| Stabilizer | 0.5-1.5 |
| Solvent | ad 100.0 |

EXAMPLE 15

From the compounds of the present invention a series of dilution is prepared in acetone; concentration 1, 0.2, 0.04, 0.008 and 0.0016%, respectively. The solutions thus obtained (0.5 ml) are poured dropwise onto Whatman No. 1. filter paper discs (diameter 90 mm) placed in Petri-dishes. After the solvent has evaporated 1-2 weeks' old bean beetle (*Acanthoscalides obtectus*) images are placed into the Petri-dishes. 3 replicates (10-15 insects each) are used for each concentration. The pesticidal effect of the test compounds is evaluated after 24 hours, on the basis of the percental ratio of the killed and paralysed individuals. The solvent control group shows no mortality. The results obtained are summarized in Table I.

| Active ingredient Example Number | Concentration of active ingredient (%) | | | | |
|---|---|---|---|---|---|
| | 1 | 0.2 | 0.04 | 0.008 | 0.0016 |
| | mortality % | | | | |
| 3 | 97 | 80 | 53 | 27 | 0 |
| 1 | 100 | 97 | 87 | 50 | 0 |
| 4 | 100 | 87 | 70 | 37 | 0 |
| 2 | 100 | 100 | 60 | 40 | 0 |
| Dioxacarb | 100 | 93 | 43 | 30 | 0 |
| Carbofuran | 100 | 100 | 100 | 93 | 0 |

EXAMPLE 16

From the test compounds a series of dilution disclosed in Example 15 is prepared whereupon 3-5 days' old house fly (*Musca domestica*) images being under slight carbon dioxide narcosis are placed onto the infected treated filter paper discs. Three replicates (10-150 flies each) are used for each concentration. The insecticidal activity of the test compounds and that of the referent compounds is evaluated after 24 hours on the basis of the percental ratio of the killed and paralyzed flies. In the solvent control grop there was no mortality. The results are summarized in Table II.

| Test compound Example Number | Concentration of active ingredient (%) | | | | |
|---|---|---|---|---|---|
| | 1 | 0.2 | 0.04 | 0.08 | 0.0016 |
| | mortality % | | | | |
| 3 | 97 | 70 | 40 | 33 | 0 |
| 1 | 100 | 80 | 43 | 40 | 30 |
| 4 | 100 | 83 | 37 | 20 | 0 |
| 2 | 90 | 67 | 30 | 10 | 0 |
| Dioxacarb | 100 | 90 | 17 | 10 | 0 |
| Carbofuran | 100 | 100 | 67 | 53 | 43 |

EXAMPLE 17

From the 2,3-dihydro-2,2-dimethyl-7-benzofuranyl-N-methyl-N-(N'-morpholinomethyl)-carbamate, dioxacarb and carbofuran series of dilutions are prepared in acetone: the active ingredient content of the solutions amounts to 40.5, 13.5, 4.5, 1.5, 0.5, 0.16 and 0.05 mg active ingredient per 3.5 μl, respectively. The solutions (0.5 μl) are applied with the aid of a Hamilton syringe onto the dorsal cuticulum of small American flour-beetle (*Tribolium confusum*) of $L_6$ larva stage. The age of the larvae is determined on the basis of the average larva weight (=1.81±0.37 mg/larva) See Sokoloff 1972.

Two replicates are used for each concentration (10 individuals per replicate). The insecticidal effect of the test compounds is evaluated after 96 hours on the basis of the percental ratio of killed larvae. The control treatment carried out with 0.5 μl pure acetone solution shows no mortality. The results obtained are summarized in Table III.

| Test compound | Dose, μg/larva | | | | | | |
|---|---|---|---|---|---|---|---|
| | 40.5 | 13.0 | 4.5 | 1.5 | 0.5 | 0.16 | 0.03 |
| | mortality % | | | | | | |
| Compound of Example 1 | 100 | 100 | 95 | 90 | 90 | 80 | 75 |
| Dioxacarb | 80 | 55 | 50 | 50 | 45 | 40 | 25 |
| Carbofuran | 100 | 100 | 100 | 100 | 100 | 70 | 30 |

EXAMPLE 18

The acute toxicity data (p.o.) of the test compounds are disclosed in Table IV.

| Test compound | on male rats | on female rats |
|---|---|---|
| | (mg/kg) | |
| 2,3-dihydro-2,2-dimethyl-7-benzofuranyl-N—methyl-N—[N'—(isopropyl)-N'—(β-carbetoxyethyl)-amino-methyl]-carbamate | 23.26 | 31.84 |
| 2,3-dihydro-2,2-dimethyl-7-benzofuranyl-N—methyl-N—(N'—morpholinomethyl)-carbamate | 50.00 | 50.00 |
| Carbofuran | 8-14 | |

EXAMPLE 19

Preparation of a starting material

To a solution of 88.8 g of 2,3-dihydro-2,2-dimethyl-7-benzofuranyl-N-methyl-carbamate and 700 ml of benzene 12.6 g of paraformaldehyde are added, whereupon 48.8 g of thionyl chloride are added dropwise within an hour. After 2 hours the solution is clarified, filtered and the solvent is evaporated. Thus 104.7 g of 2,3-dihydro-2,2-dimethyl-7-benzofuranyl-N-methyl-N-chloromethyl-carbamate are obtained, mp.: 115°–118° C.

Analysis: for the Formula $C_{13}H_{16}ClNO_3$

| calculated: | C = 57.88% | H = 5.94% | N = 5.19% | Cl = 13.17% |
|---|---|---|---|---|
| found: | C = 57.67% | H = 6.17% | N = 5.22% | Cl = 12.06%. |

EXAMPLE 20

Preparation of granules

3% by weight of 2,3-dihydro-2,2-dimethyl-7-benzofuranyl-N-methyl-N-(N'-morpholinomethyl)-carbamate
6% by weight of piperonyl butoxide
15% by weight of dimethyl formamide and
76% by weight of furfurol bran (particle size 0.2–1 mm)
are admixed.

Granules having the following composition are prepared:

| Component | Amount (% by weight) |
|---|---|
| Active ingredient | 1–10 |
| Piperonyl butoxide | 2–20 |
| Solvent | 5–20 |
| Carrier | ad 100 |

EXAMPLE 21

Emulsifiable concentrate

20% by weight of 2,3-dihydro-2,2-dimethyl-7-benzofuranyl-N-methyl-N-(N'-morpholinomethyl)-carbamate
15% by weight of piperonyl butoxide
7% by weight of ATLOX 3276 FLN and
58% by weight of xylene
are admixed.

The emulsifiable concentrate thus obtained has the following composition:

| Component | Amount (% by weight) |
|---|---|
| Active ingredient | 5–30 |
| Piperonyl butoxide | 10–30 |
| Ionic and non-ionic surfactant | 5–15 |
| Solvent | ad 100. |

EXAMPLE 22

Determination of synergistic effect

From the compound according to Example 1 a series of dilution is prepared in acetone; concentration: 0.6, 0.2, 0.067 and 0.022% by weight, respectively. From these solutions 0.5 ml each is poured dropwise onto Whatman No. 1 filter paper discs (diameter 90 mm) placed in Petri-dishes. The discs were previously treated with 0.5 ml of a 0.04% piperonyl butoxide solution. After the evaporation of the acetone 3–5 days' old house fly (*Musca domestica*) imagos being under slight carbon dioxide narcosis are placed onto the filter paper discs. The test is evaluated as described in Example 16. The results are summarized in Table V.

| Test compound | Concentration of active ingredient (%) | | | |
|---|---|---|---|---|
| | 0.6 | 0.2 | 0.067 | 0.022 |
| | mortality % | | | |
| Compound according to Example 1 | 100 | 100 | 78 | 32 |
| Compound according to Example 1 + piperonylbutoxide | 100 | 100 | 100 | 69 |
| Carbofuran | 100 | 100 | 100 | 71 |

EXAMPLE 23

Determination of systemic effect

The granules prepared according to Example 13 (active ingredient content 5%) are spread out in an amount corresponding to a dose of 15 kg/ha and 7.5 kg/ha, respectively, into flower pots filled with soil, whereupon seeds of broad bean (*Vicia faba*) are sown into the soil. The plants are infected with plant louse (*Megaure viciae*) placed into leaf isolator at a 2 weeks' age. Twenty insects are used for each isolator. The percental mortality is evaluated after 48 hours. The data obtained are summarized in Table VI.

|  | Dose | |
| --- | --- | --- |
| Test compound | 15 kg/ha | 7.5 kg/ha |
|  | mortality % | |
| Compound according to Example 13 | 100 | 38 |
| CHINUFUR 5 G | 100 | 56 |
| Untreated control | 0 | 0 |

What is claimed is:

1. A compound of the Formula I

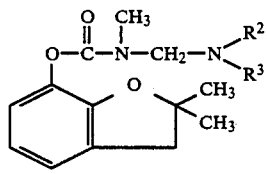

or a salt thereof, wherein
R$^2$ stands for hydrogen or C$_{1-4}$ alkyl; and
R$^3$ represents a group of the Formula R$^4$-(CH$_2$)$_n$- wherein
n is 1 or 2;
R$^4$ represents C$_1$ to C$_4$ alkoxy-carbonyl or a group of the Formula II,

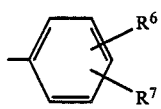

and
R$^6$ and R$^7$ stand for C$_{1-4}$ alkoxy.

2. A compound of the Formula (I)

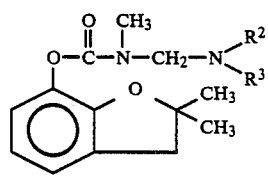

or a salt thereof, wherein
R$^2$ is hydrogen or C$_1$ to C$_4$ alkyl;
R$^3$ is a group of for Formula R$^4$—(CH$_2$)$_n$— wherein n is 1 or 2; and
R$^4$ is C$_1$ to C$_4$ alkoxy-carbonyl.

3. A compound of the Formula (I)

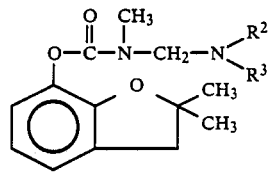

or a salt thereof, wherein
R$^2$ is hydrogen or C$_1$ to C$_4$ alkyl;
R$^3$ is a group of the Formula R$^4$—(CH$_2$)$_n$— wherein n is 1 or 2;
R$^4$ is a group of the Formula (II)

and
R$^6$ and R$^7$ are each C$_1$ to C$_4$ alkoxy.

4. 2,3-dihydro-2,2-dimethyl-7-benzofuranyl-N-methyl-N-[(N'-isopropyl)-N'-(β-carbethoxy-ethyl)-aminomethyl]-carbamate or a salt thereof as defined in claim 1.

5. 2,3-dihydro-2,2-dimethyl-7-benzofuranyl-N-methyl-N-[β-3,4-dimethoxy-phenyl-ethyl)-amino-methyl]-carbamate or a salt thereof as defined in claim 1.

6. Pesticidal composition comprising as active ingredient a pesticidally effective amount of a compound of the Formula I

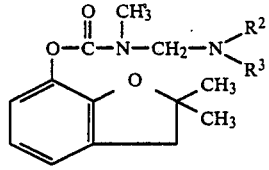

wherein
R$^2$ stands for hydrogen or C$_{1-4}$ alkyl; and
R$^3$ represents a group of the Formula R$^4$—(CH$_2$)$_n$—
wherein n is 1 or 2;
R$^4$ represents C$_1$ to C$_4$ alkoxy carbonyl
or a group of the Formula II

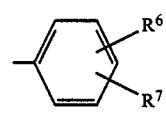

and
R$^6$ and R$^7$ stand for C$_{1-4}$ alkoxy;
or a salt thereof, in admixture with a suitable auxiliary agent.

7. Pesticidal composition according to claim 6 in the form of a suspension concentrate comprising as active ingredient 1–60% by weight of a compound of the Formula I or a salt thereof in admixture with suitable auxiliary agents and optionally further active ingredient(s).

8. Suspension concentrate according to claim 7 comprising 1–10% by weight of a surfactant as auxiliary agent.

9. Dispersible granular composition according to claim 6 comprising as active ingredient 1–99% by weight of a compound of the Formula I or a salt thereof in admixture with suitable auxiliary agents.

10. Dispersible granular composition according to claim 9 comprising 0.1–10% by weight of an anionic and/or nonionic surfactant as auxiliary agent.

11. Granular composition according to claim 6 comprising as active ingredient in an amount of 1–20% by weight a compound of the Formula I or a salt thereof in admixture with 80–99% by weight of suitable auxiliary agents and optionally further active ingredient(s) and/or synergist(s).

12. Granular composition according to claim 11 comprising an adhesive, coloring agent and/or carrier as auxiliary agent.

13. Granular composition according to claim 11 comprising piperonyl butoxide as synergist.

14. Emulsifiable concentrate according to claim 6 comprising as active ingredient in an amount of 10–50% by weight a compound of the Formula I or a salt thereof in admixture with suitable auxiliary agents suitable to form a stable emulsion and optionally further active ingredient(s) and/or synergist(s).

15. Emulsifiable concentrate according to claim 14 comprising as auxiliary agent 1–20% by weight of tenside and/or 0.1–5% by weight of a stabilizer and a solvent up to 100% by weight.

16. Emulsifiable concentrate according to claim 14 comprising piperonyl butoxide as synergist.

17. Method for combating insect pests and for inhibiting the growth thereof which comprises contacting the insects at optional growth stage with a pesticidally effective amount of at least one compound as defined in claim 1 or a salt thereof or a composition comprising the same, on a plant or in the soil.

* * * * *

UNITED STATES PATENT AND TRADEMARK OFFICE
CERTIFICATE OF CORRECTION

PATENT NO. : 4,788,217
DATED : 29 November 1988
INVENTOR(S) : Gyorgy LANYI et al It is certified that error appears in the above-identified patent and that said Letters Patent is hereby corrected as shown below: Title page:

Item [75] Inventors' names are to read:

First name of the first inventor is to read:
-- Gyorgy --;

Last name of the fifth inventor is to read:
-- Hegedus --;

First name of the sixth inventor is to read:
-- Laszlo --.

Signed and Sealed this

Eighteenth Day of April, 1989

*Attest:*

DONALD J. QUIGG

*Attesting Officer*  *Commissioner of Patents and Trademarks*